(12) United States Patent
Beck et al.

(10) Patent No.: US 9,179,542 B2
(45) Date of Patent: Nov. 3, 2015

(54) ARTICLES CONTAINING NON-VISIBLE IDENTIFYING MARKS FORMED FROM NANOMATERIALS AND METHODS UTILIZING THE SAME

(71) Applicant: LOCKHEED MARTIN CORPORATION, Bethesda, MD (US)

(72) Inventors: Michael S. Beck, Clifton, VA (US); Hilary S. Lackritz, Sunnyvale, CA (US); Jonathan W. Ward, San Jose, CA (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 14/256,840

(22) Filed: Apr. 18, 2014

(65) Prior Publication Data
US 2014/0312248 A1 Oct. 23, 2014

Related U.S. Application Data

(60) Provisional application No. 61/815,232, filed on Apr. 23, 2013.

(51) Int. Cl.
*G01N 21/64* (2006.01)
*H05K 1/02* (2006.01)
(Continued)

(52) U.S. Cl.
CPC ............ *H05K 1/0275* (2013.01); *G01N 21/643* (2013.01); *G01N 21/65* (2013.01); *B82Y 30/00* (2013.01); *G01N 2021/6417* (2013.01);
(Continued)

(58) Field of Classification Search
CPC .................................................... H01F 1/0045

USPC ........................................................ 250/459.1
See application file for complete search history.

(56) References Cited

U.S. PATENT DOCUMENTS 7,572,426 B2    8/2009  Strano et al.
7,821,079 B2 *  10/2010 Cho et al. ...................... 257/379
(Continued)

FOREIGN PATENT DOCUMENTS

CN         103018231 A  *  4/2013
WO      WO-2013/100794 A1    7/2013

OTHER PUBLICATIONS

F. Beuneu, "Nucleation of single wall carbon nanotubes of various chiralities," 2012, Solid State Communications, vol. 152, pp. 1155-1159.*

(Continued)

*Primary Examiner* — Kiho Kim
(74) *Attorney, Agent, or Firm* — McDermott Will & Emery LLP

(57) ABSTRACT

Identifying marks are often used for authentication and tracking purposes with various types of articles, but they can sometimes be subject to replication or removal by an outside entity, such as a person or group having malicious intent. Carbon nanotubes and other carbon nanomaterials can be used to form identifying marks that are not visible to the naked eye, thereby making the marks more difficult for an outside entity to tamper with. Various articles can include an identifying mark that is not visible to the naked eye, the identifying mark containing a nanomaterial that includes a plurality of carbon nanotubes with a registered distribution of chiralities. The registered distribution of chiralities can be further tailored to increase the level of security provided by the mark.

15 Claims, 8 Drawing Sheets

(51) Int. Cl.
   *G01N 21/65* (2006.01)
   *B82Y 30/00* (2011.01)
(52) U.S. Cl.
   CPC ...... *G01N2021/6439* (2013.01); *H05K 1/0266* (2013.01); *H05K 2201/026* (2013.01); *H05K 2201/09927* (2013.01); *Y10S 977/932* (2013.01); *Y10T 428/24851* (2015.01); *Y10T 428/24893* (2015.01)

(56) References Cited

U.S. PATENT DOCUMENTS

2005/0156318 A1*   7/2005   Douglas ................... 257/761
2008/0276817 A1*  11/2008   Hinch et al. .............. 101/491
2010/0059595 A1    3/2010   Longfu
2010/0061619 A1*   3/2010   Boegli .................... 382/141
2010/0209632 A1*   8/2010   Weisman et al. .......... 428/29
2014/0205083 A1    7/2014   Pryakhin et al.

OTHER PUBLICATIONS

Ortolani et al., "Chirality dependent surface adhesion of single-walled carbon nanotubes on graphene surfaces," 2010, Carbon, vol. 48, pp. 3050-3056.*

Bachilo, et al., "Structure-assigned optical spectra of single-walled carbon nanotubes," ACS Nano, 2002, pp. 2361-2366, vol. 298.

* cited by examiner

ARTICLES CONTAINING NON-VISIBLE IDENTIFYING MARKS FORMED FROM NANOMATERIALS AND METHODS UTILIZING THE SAME

CROSS-REFERENCE TO RELATED APPLICATIONS

This application claims the benefit of priority under 35 U.S.C. §119 from U.S. Provisional Patent Application 61/815,232, filed Apr. 23, 2013, which is incorporated herein by reference in its entirety.

STATEMENT REGARDING FEDERALLY SPONSORED RESEARCH OR DEVELOPMENT

Not applicable.

FIELD

The present disclosure generally relates to carbon nanomaterials, and, more specifically, to methods for tracking and authenticating articles using carbon nanomaterials, particularly carbon nanotubes.

BACKGROUND

Millions of dollars are lost annually by manufacturers due to the theft or misdirection of shipments of consumer goods. An even greater problem for manufacturers in many industries is the growing prevalence of counterfeit reproductions of their products. Counterfeit products can be problematic for a manufacturer in terms of lost revenue Low quality counterfeit products can also unfairly taint the reputation of a manufacturer in the public's eyes, particularly if the public is unaware that a counterfeiting problem exists.

Tampering of articles by an outside entity attempting to reverse-engineer or alter the articles represents a significant concern for manufacturers. As used herein, the terms "tamper," "tampering," and other grammatical equivalents thereof will refer to any unauthorized use, access, investigation or alteration of an article, whether malicious or not. A number of anti-tampering protocols are often put into place by manufacturers to restrict an outside entity's ability to determine the true operational principles of an article. Particularly in the electronics industry, tampering represents an ongoing challenge for manufacturers. Some anti-tampering protocols focus on masking the true operational principles of an article, thereby making it difficult for an outside entity to reverse-engineer the article and produce a counterfeit copy.

Tampering can also involve removing, altering or replicating an identifying mark that serves to verify the authenticity of an article. The terms "mark," "tag" and grammatical equivalents thereof may be used synonymously herein. Removing, altering or replicating an identifying mark can be problematic from standpoints of both theft and counterfeiting. A number of identifying marks have been routinely used for tagging various articles, including bar codes, RFIDs, and the like. However, these types of identifying marks are often readily visible to an outside entity. With enough diligence, they can often be copied by an outside entity for marking counterfeit articles in much the same way as an authentic article. Likewise, removal, alteration, or replacement of an identifying mark from an authentic article can make the article untrackable and subject to theft.

In view of the foregoing, there remains a need to develop identifying marks providing an enhanced level of security. The present disclosure satisfies the foregoing need and provides related advantages as well.

SUMMARY

In various embodiments, articles described herein can include an identifying mark that is not visible to the naked eye. In some embodiments, the identifying mark contains a nanomaterial that includes a plurality of carbon nanotubes having a registered distribution of chiralities. In some or other embodiments, the identifying mark contains a carbon nanomaterial and is spectroscopically identifiable.

In various embodiments, methods described herein can include providing an article in need of tracking; applying an identifying mark to a surface of the article; operationally deploying the article; and after operationally deploying the article, optically interrogating the article with electromagnetic radiation to assay the identifying mark. The identifying mark is not visible to the naked eye and contains a nanomaterial that includes a plurality of carbon nanotubes having a registered distribution of chiralities The foregoing has outlined rather broadly the features of the present disclosure in order that the detailed description that follows can be better understood. Additional features and advantages of the disclosure will be described hereinafter These and other advantages and features will become more apparent from the description below taken in conjunction with the drawings.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION

Figure 1:
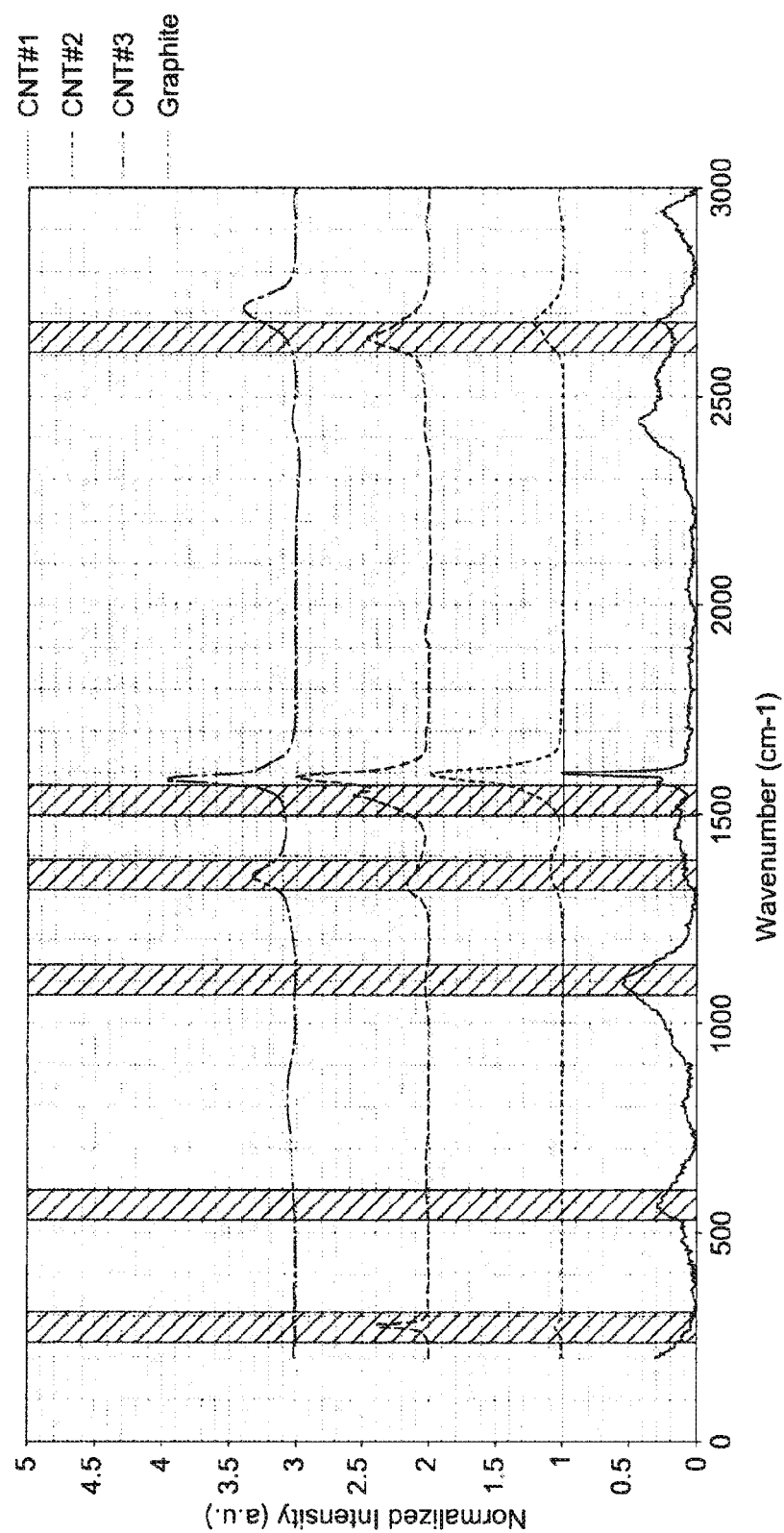
FIG. 1 shows a series of illustrative Raman spectra of various carbon nanotube samples that differ slightly in their chiral distribution.

The present disclosure is directed, in part, to articles with an identifying mark formed from a nanomaterial, particularly those that contain carbon nanotubes having a registered distribution of chiralities, the identifying mark not being visible to the naked eye. The present disclosure is also directed, in part, to methods for tagging various articles with an identifying mark formed from a nanomaterial that includes carbon nanotubes having a registered distribution of chiralities, the identifying mark not being visible to the naked eye.

Although applying an identifying mark to various articles can often constitute a portion of a manufacturer's anti-tampering protocols, many types of marks are themselves subject to illicit copying or alteration, thereby defeating the purpose of the mark. In many instances, such marks are readily viewable by an outside entity with malicious intent, thereby providing an alert that the mark must also be replicated in producing a counterfeit article that is harder to identify. In the case of theft, a visible mark can alert an outside entity that the mark needs to be removed to prevent tracking of the stolen goods. Although identifying marks can be hidden from view or embedded within an article to preclude their observation by an outside entity, surveying the article to determine if it is marked can then become much more problematic in certain instances. In some cases, it might even be necessary to damage the article to expose the mark, which can be particularly undesirable.

The present inventors recognized that carbon nanotubes or other carbon nanomaterials, optionally in combination with other types of carbonaceous materials, could be used in marking and tracking applications to provide significant advantages over conventionally used identifying marks. More specifically, the inventors recognized that the distinct spectroscopic properties of carbon nanotubes could be leveraged to provide identifying marks with unique spectral signatures that are not easily replicable by an outside entity. In this regard, carbon nanotubes offer a number of advantages, as discussed below. Other carbon nanomaterials can also provide similar advantages.

Foremost, the spectroscopic properties of carbon nanotubes vary in an identifiable manner based upon, among other features, their chirality, thereby allowing a carbon nanotube spectrum to be resolved into both the types and abundances of the various carbon nanotube chiralities that are present in a sample. Carbon nanotube chirality refers to the orientation of carbon-carbon bonds within a carbon nanotube, as described in more detail below. By providing a population of carbon nanotubes with a known or registered distribution of carbon nanotube chiralities, an identifying mark can be produced therefrom with a unique spectral fingerprint that is very difficult for an outside entity to replicate, even if they know that carbon nanotubes are present in the article at all. In this regard, carbon nanotube synthetic conditions can often be varied to alter the distribution of carbon nanotube chiralities obtained, thereby offering the opportunity to tailor the spectral fingerprint of an identifying mark formed therefrom in a manner that may only be known and/or reproduced by an authorized entity. In another aspect, designed populations of carbon nanotubes can be formulated by combining carbon nanotubes from different carbon nanotube synthetic processes, thereby providing access to custom chirality distributions that may not be attainable directly from a single carbon nanotube synthetic process. In still another aspect, a population of carbon nanotubes can be treated to remove certain carbon nanotube chiralities following a carbon nanotube synthesis, thereby enriching the population of carbon nanotubes in the remaining chiralities. The removed carbon nanotubes can be similarly enriched in one or more chiralities. Functionalization of the carbon nanotubes can also be used to further tailor the spectral properties as needed. In summary, numerous options are available to make a population of carbon nanotubes difficult to replicate by an outside entity attempting to form an identifying tag therefrom.

Even if the size, shape and location of an identifying mark containing carbon nanotubes is determined and replicated by an outside entity, it can be exceedingly difficult for the outside entity to precisely match the specific distribution of carbon nanotube chiralities that is present in the mark. For example, an outside entity might attempt to replicate an identifying mark to contain a like percentage of carbon nanotubes having a dominant chirality, but in doing so, it may not be possible for the outside entity to match the percent abundance of another type of carbon nanotube having a different chirality That is, without knowing how the population of carbon nanotubes in the identifying mark was formed or further processed, it can be difficult for an outside entity to replicate the relative abundances of various carbon nanotube chiralities within the mark.

As a further advantage of carbon nanotubes in marking applications, carbon nanotubes are commonly present in various articles to take advantage of the enhancements conveyed by their mechanical, electrical and thermal properties. That is, the presence of carbon nanotubes in certain types of articles is not to be unexpected, and it can be difficult for the outside entity to even locate the mark at all. Thus, in some embodiments, an identifying mark formed from carbon nanotubes with a registered distribution of chiralities can be effectively "hidden" within another population of carbon nanotubes having either unregistered chiralities or a different distribution of chiralities compared to the identifying mark. Similarly, an identifying mark formed from carbon nanotubes can by effectively "hidden" within other carbonaceous materials such as graphene, diamond, polymers, polyaromatic hydrocarbons and the like. Carbon nanomaterials other than carbon nanotubes can also provide similar advantages in this regard. Only by locating the "hidden" identifying mark and conducting detailed analyses of it would an outside entity potentially come to realize its true purpose. Even then, replication of such identifying marks can be difficult for the reasons discussed herein. Further, as noted above, the identifying marks described herein are not considered to be visible to the naked eye, so they can be effectively "hidden" in plain sight.

In addition to producing identifying marks with a unique spectral fingerprint through tailoring of the chirality distribution, carbon nanotubes also offer significant advantages due to their extreme detection sensitivity. Fluorescence spectroscopy and Raman spectroscopy, the two spectral techniques most often used for determining carbon nanotube chiralities, are extremely sensitive when used for detecting carbon nanotubes. As a result, identifying marks containing very low carbon nanotube levels can be applied to an article and still remain detectable, even if the identifying mark is not visible to the naked eye, Identifying marks of very small physical dimensions can also provide like advantages.

Similar to fluorescence and Raman spectroscopies, the non-linear optical properties of carbon nanotubes can be used for assaying the particular characteristics of a population of carbon nanotubes. Specifically, by impinging a first wavelength of electromagnetic radiation upon the carbon nanotubes and receiving a second wavelength of altered frequency from the carbon nanotubes, it can be determined what types of carbon nanotubes are present by measuring the frequency shift. Thus, by making use of the non-linear optical properties of carbon nanotubes, an identifying mark with a distinctive spectral signature characteristic of the carbon nanotubes therein can similarly be obtained.

In additional embodiments, various addends can also be included in the carbon nanotubes or other carbon nanomaterial to convey a characteristic reflectivity signature to the identifying mark. Further, the carbon nanotubes or other carbon nanomaterials in the identifying mark can also be patterned, if desired, to create a frequency selective surface that can act as an optical bandpass filter during its interrogation with electromagnetic radiation. Either of these features can convey an additional level of security to the identifying marks.

Finally, identifying marks containing carbon nanotubes or other carbon nanomaterials can be either active or passive within an article in which they provide their tagging function.

In passive tagging applications, the carbon nanotubes or carbon nanomaterials do not meaningfully contribute to the operational function of the article and only serve as a detectable identifying mark. In active tagging applications, the carbon nanotubes or carbon nanomaterials can provide at least one additional function within the article in addition to their tagging function. For example, an active mark can contribute to structural reinforcement within at least a portion of an article, or an active mark can constitute at least a portion of an electrically conductive pathway within an article. When serving within an electrically conductive pathway, tailoring of the distribution of carbon nanotube chiralities within the mark can also alter the operational function of the article, if desired. For example, depending upon if one wants to produce a conductive or semiconductive electrical connection within an article, one can formulate a population of carbon nanotubes to have chiralities that lead to either semiconducting or metallic conductivity. The opportunity to alter the operational function of an article without visually changing its appearance can convey another level of tamper resistance thereto.

As used herein, the term "identifying mark" or just "mark" refers to a region that contains carbon nanotubes upon or within an article, such that the carbon nanotubes can be optically interrogated to receive a signal therefrom. Other carbon nanomaterials can be used similarly in this regard. Within the context of the present embodiments, marks are not particularly limited in size, shape, thickness, or the like, unless otherwise indicated herein. In various embodiments, the marks described herein can be "invisible" or "not visible to the naked eye." In alternative embodiments, however, such marks can remain visible to the naked eye As used herein, the term "optically interrogate" and variants thereof refers to the interaction of electromagnetic radiation of any wavelength with a carbon nanomaterial and receipt and analysis of the electromagnetic radiation thereafter.

As used herein, the term "not visible to the naked eye" refers to a mark that cannot be seen with the human eye under ordinary circumstances, including through optical enhancement, such as with a microscope or like optical magnifier. For the purposes of this disclosure, identifying marks that cannot be seen with an optical microscope under ordinary circumstances will be considered to be "not visible to the naked eye." Identifying marks that are not visible to the naked eye can be "spectroscopically identifiable" however.

As used herein, the term "registered distribution of chiralities" refers to a population of carbon nanotubes having a chirality distribution that is known to a limited number of entities, but is unknown to an outside entity.

As used herein, the term "carbon nanotube chirality" refers to a double index (n,m) describing a particular carbon nanotube, where n and m are integers that describe the cut and wrapping of hexagonal graphite when formed into a tubular structure. Such designation of a carbon nanotube's chirality will be familiar to one having ordinary skill in the art. As used herein, the term "semiconducting carbon nanotube" refers to a carbon nanotube that is defined by the relationship $|m-n|=3k+1$, where k is an integer. As used herein, the term "metallic carbon nanotube" refers to a carbon nanotubes that is defined by the relationship $|m-n|=3k$, where k is an integer. According to the embodiments of the present disclosure, metallic carbon nanotubes and semi-metallic carbon nanotubes will be considered to be synonymous with one another. Carbon nanotubes may be further characterized as being "zigzag chirality" or "armchair chirality" based upon their chiral indices. For example, metallic carbon nanotubes having m n are characterized as "armchair chirality" carbon nanotubes.

As used herein, the term "operationally deploying" refers to the condition that exists when an article is released from its manufacturer's control. In some embodiments, an article can be considered to be operationally deployed when the article is passed from a manufacturer to a retailer or wholesaler, or directly provided to a consumer or industrial project. In some or other embodiments, an article can be considered to be operationally deployed when the article is situated in its intended operational location. In any event, a manufacturer or other entity may wish to interrogate the article after its deployment in order to verify the article's authenticity. Not only can such analyses help a manufacturer identify counterfeit articles, but they can also provide improved consumer safety by identifying counterfeit articles that are deployed in various mission-critical situations.

As used herein, the term "non-native distribution of chiralities" refers to a chirality distribution that is generally not attainable directly from a carbon nanotube synthetic process.

As used herein, the term "tracking" will refer to a process of identification or authentication. The terms "tagging," "tracking" and related variants thereof will be used synonymously herein.

In some embodiments, articles described herein can include an identifying mark that is not visible to the naked eye, where the identifying mark contains a carbon nanomaterial that includes a plurality of carbon nanotubes having a registered distribution of chiralities. FIG. 1 shows a series of illustrative Raman spectra of various carbon nanotube samples that differ slightly in their chiral distribution. As can be seen in FIG. 1, slight spectral shifts can be observed, and the spectral peaks can be differentiated from those of graphite.

In some embodiments, the identifying mark can include substantially a monolayer of carbon nanotubes on a surface of the article. In various embodiments, a monolayer of carbon nanotubes is not to be visible to the naked eye but can remain detectable by various spectroscopic techniques. Thicker carbon nanotube layers can also remain invisible to the naked eye and can be used in some embodiments of the present disclosure.

In some embodiments, the identifying mark can remain invisible to the naked eye due to a coating that covers at least the identifying mark of the article. Suitable coatings are described in more detail below. In some embodiments, the article itself or the coating can further include another carbonaceous material which can also mask the presence of the carbon nanotubes or other carbon nanomaterial and render them not visible to the naked eye. Carbonaceous materials that can mask the presence of carbon nanotubes can include, for example, graphite, graphene, amorphous carbon, carbon black, polymers, polyaromatic hydrocarbons, and the like. Some of these entities can be used to further tailor the spectral signature produced by the identifying mark, as shown in FIGS. 3A-3C and 4A-4C below.

In general, carbon nanotubes and other carbon nanomaterials adhere fairly readily to a variety of surface types. Accordingly, the types of articles that can be marked according to the embodiments described herein are not believed to be particularly limited. Illustrative articles that can be marked by applying carbon nanotubes having a registered distribution of chiralities thereto include, for example, electrical devices, circuit boards, jewelry, automobiles, medical devices, sporting goods, structural components, mirrors, lenses, optical filters, various components thereof, and the like In some embodiments, the identifying mark can be applied to the article itself, and in other embodiments, the identifying mark can be applied to the packaging in which one or more articles are being shipped. In still other embodiments, the identifying mark can be present within the article itself.

Although any type of article can be marked according to the embodiments described herein, it is believed that marking of electrical devices can be particularly advantageous. As indicated above, many types of electrical devices containing carbon nanotubes are in development. Thus, an identification mark containing carbon nanotubes, either visible or non-visible, can be incorporated within such devices without alerting an outside entity of the mark's presence. For example, an identifying mark having a registered distribution of carbon nanotube chiralities can be incorporated within a larger population of carbon nanotubes with a different chirality distribution, which may or may not be used to alter the operational principles of the electrical device. In such embodiments, the identifying mark can be electrically isolated from the larger population of carbon nanotubes, electrically connected to the larger population of carbon nanotubes without changing the operational principles of the electrical device (i.e., as a "dummy" electrical pathway), or overlay a portion of the larger population of carbon nanotubes in an electrical circuit. In the latter configuration, the region of the electrical circuit containing the identifying mark can only be distinguished from the remainder of the electrical circuit by knowing the location of the mark and determining its unique spectral signature. In still further configurations, the identifying mark can itself contribute to the electrical operational principles of the device by establishing a conductive or semiconductive pathway therein based on the particular carbon nanotube chirality distribution that is present in the mark. Thus, in some embodiments, an identifying mark formed from carbon nanotubes can be used to establish "invisible" electrical connections within an electrical device in order to mask the device's true electrical operational principles, thereby making reverse engineering much more difficult for an outside entity.

In some embodiments, the article can include an electrical device. The type of electrical device being marked with carbon nanotubes according to the present embodiments is not believed to be particularly limited. For example, in various embodiments, the electrical device can include a two-terminal electrical device or a three-terminal device (e.g., a gated electrical device). In some embodiments, the plurality of carbon nanotubes having a registered distribution of chiralities can constitute at least a portion of a conductive line in a circuit of the electrical device. In some embodiments, the conductive line can be formed entirely with carbon nanotubes having a registered distribution of chiralities, and in other embodiments, one or more separated regions of the conductive line can be formed with carbon nanotubes having a registered distribution of chiralities. Either of these configurations would appear the same to the naked eye of an outside entity, or not visible to the naked eye at all according to some embodiments.

The plurality of carbon nanotubes having a registered distribution of chiralities can be produced by any suitable technique. Suitable carbon nanotube synthetic processes can include, for example, arc methods, laser oven, chemical vapor deposition, flame synthesis, and high pressure carbon monoxide (HiPCO). The synthetic conditions of any of these techniques can be altered to change the chirality distribution produced, particularly to favor the production of carbon nanotubes with a dominant carbon nanotube chirality or type being produced.

In some embodiments, the plurality of carbon nanotubes in the identifying mark can constitute as-produced carbon nanotubes obtained from a carbon nanotube synthetic process. As discussed above, one practicing the embodiments described herein can choose carbon nanotubes produced by a particular carbon nanotube synthetic process based upon the distribution of carbon nanotube chiralities obtained under a specific set of carbon nanotube synthetic conditions. Optionally, the carbon nanotubes can be further purified, such as by acid treatment to remove at least a portion of a residual transition metal carbon nanotube growth catalyst from the carbon nanotubes. In some embodiments, an amount of residual transition metal carbon nanotube growth catalyst within an identifying mark can be determined and compared against the value of this quantity in the carbon nanotubes used to apply the mark to an article. Thus, analysis of the residual transition metal carbon nanotube growth catalyst within an identifying mark can serve as a secondary level of authentication in addition to the distribution of carbon nanotube chiralities.

In some or other embodiments, the plurality of carbon nanotubes having a registered distribution of chiralities can include a mixture of carbon nanotubes combined from a first carbon nanotube synthetic process and a second carbon nanotube synthetic process, where the first and second carbon nanotube synthetic processes produce carbon nanotubes that differ in at least their distribution of chiralities. That is, the plurality of carbon nanotubes having a registered distribution of chiralities can be formed by combining, in any ratio, two different batches of carbon nanotubes, each with its own unique chirality distribution. For example, a first carbon nanotube synthetic process may produce a majority amount of a first carbon nanotube chirality [e.g., (6,5) chirality] and lower amounts of one or more second carbon nanotube chiralities [e.g., (7,5) and (8,4) chiralities], and a second carbon nanotube synthetic process may produce a majority amount of one or more of the second carbon nanotube chiralities or a different set of carbon nanotube chiralities entirely. By combining carbon nanotubes from the first and second carbon nanotube synthetic processes, a plurality of carbon nanotubes having a distinctive chirality signature can be formulated for preparing an identifying mark. Such chirality signatures may not be directly obtainable from a single carbon nanotube synthetic process. Further, by varying the ratios of the carbon nanotubes being combined from each carbon nanotube synthetic process, the relative abundance of the various carbon nanotube chiralities to one another can be further tailored. In various embodiments, an amount of carbon nanotubes being combined from each carbon nanotube synthetic process can represent about 10% or more of the mixture, more typically about 20% or more. In some embodiments, carbon nanotubes from three or more different carbon nanotube synthetic processes can be combined with one another in a like manner.

In still other embodiments, the plurality of carbon nanotubes can include carbon nanotubes having one or more chiralities that have been enriched from as-produced carbon nanotubes obtained from a carbon nanotube synthetic process. Enrichment of particular types or chiralities of carbon nanotubes can be accomplished in various ways. In some embodiments, separation techniques based on the electrical properties of the carbon nanotubes can be used to affect separation. For example, electrophoresis can be used to separate metallic carbon nanotubes from semiconducting carbon nanotubes. Density gradient chromatography can be used similarly to separate carbon nanotubes having various chiralities from one another. Either the separated carbon nanotubes or the residual carbon nanotubes depleted of particular chiralities can be used in accordance with the embodiments described herein. In some embodiments, separating particular carbon nanotube chiralities from one another can involve selectively functionalizing carbon nanotubes having certain chiralities within a population of as-produced carbon nanotubes. For example, by controlling the reactive stoichiometry, metallic carbon nanotubes can be functionalized in preference to semiconducting carbon nanotubes, thereby allowing the two types of carbon nanotubes to be at least partially separated from one another based upon the change in properties that occur following functionalization (e.g., solubility). Some illustrative carbon nanotube functionalization techniques are discussed below. Combinations of the foregoing separation techniques can be used as well.

In some embodiments, the plurality of carbon nanotubes forming the identifying mark can be functionalized. The type of functionalization on the carbon nanotubes is not believed to be particularly limited. Illustrative carbon nanotube functionalization techniques will be familiar to one having ordinary skill in the art. In some embodiments, functionalization can be used to facilitate at least partial separation of different carbon nanotube types from one another, as alluded to above. Specifically, in some embodiments, metallic and semi-metallic carbon nanotubes can be functionalized (e.g., with a diazonium moiety as described in U.S. Pat. No. 7,572,426, which is incorporated herein by reference in its entirety) in preference to semiconducting carbon nanotubes and undergo separation from the latter based on one or more property changes following functionalization. In other embodiments, the different carbon nanotube types can be functionalized with the same functionalizing species in a non-specific manner, although not necessarily with the same degree of functionalization. In still other embodiments, semiconducting carbon nanotubes can be differentially functionalized from metallic carbon nanotubes in a plurality of carbon nanotubes used for forming an identifying mark, That is, in some embodiments, metallic carbon nanotubes can be reacted initially with a first functionalizing species, and the semiconducting carbon nanotubes can thereafter be reacted with a second functionalizing species. As indicated above, in some embodiments, the semiconducting carbon nanotubes can be separated from the functionalized metallic carbon nanotubes before undergoing functionalization with the second functionalizing species. Functionalized semiconducting carbon nanotubes can be recombined with metallic carbon nanotubes functionlized with the first functionalizing species, or they can be recombined with other metallic carbon nanotubes (including unfunctionalized metallic carbon nanotubes) or semiconducting carbon nanotubes (including unfunctionalized semiconducting carbon nanotubes) in some embodiments.

Figure 2A:
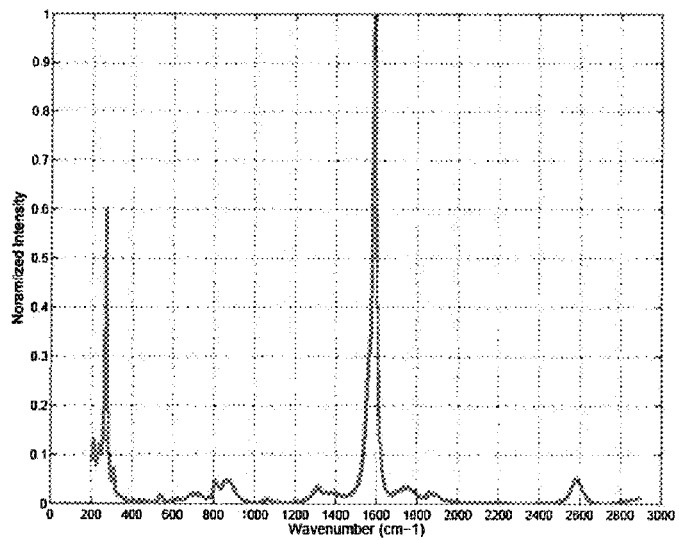
FIGS. 2A and 2B show a comparison between illustrative Raman spectra for unfunctionalized carbon nanotubes and those that have been functionalized with tetracyanoquinodimethane (TCNQ)
Figure 2B:
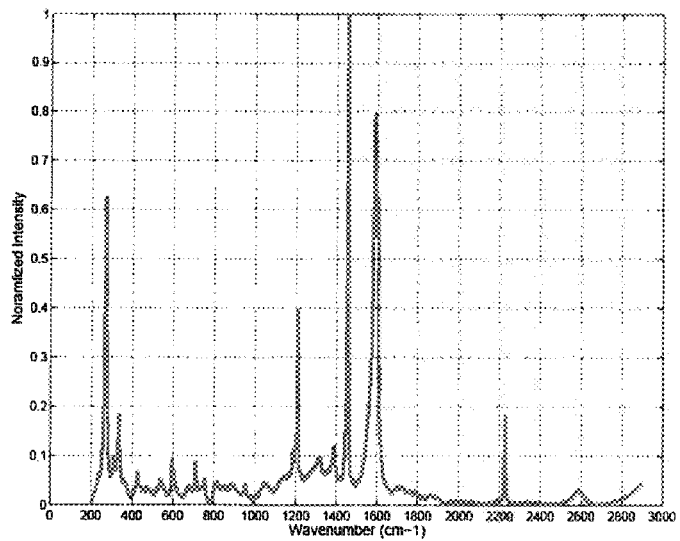

In some or other embodiments, functionalization of carbon nanotubes need not necessarily be used to separate carbon nanotube types from one another or even be specific to a particular type of carbon nanotube. In some embodiments, additional processing of the carbon nanotubes can take place to affect functionalization of the carbon nanotubes, such as plasma exposures and other relatively non-specific functionalization strategies. When performed, functionalization can take place on the ends of the carbon nanotubes, the sidewalls of the carbon nanotubes, or both. As an illustrative carbon nanotube functionalization technique, carbon nanotube ends can be opened through treatment with an appropriate oxidizing agent (e.g., $HNO_3/H_2SO_4$) to generate carboxylic acid-functionalized carbon nanotubes. Functionalization can change the spectral properties of the carbon nanotubes and shift the spectral fingerprint observed in an identifying mark formed therefrom, thereby providing a further variable that an outside entity would need to replicate in forming a counterfeit mark. For example, FIGS. 2A and 2B show a comparison between illustrative Raman spectra for unfunctionalized carbon nanotubes and those that have been functionalized with tetracyanoquinodimethane (TCNQ). As can be seen in FIG. 2B, the TCNQ peaks are prevalent in the spectrum, and the lower intensity carbon nanotube peaks have disappeared or shifted as well.

As indicated above, the particular process conditions used for preparing a batch of carbon nanotubes can often result in certain carbon nanotube chiralities being predominant, as well as differing relative abundances of the various carbon nanotube chiralities with respect to one another. It should be noted, however, that the presence of a predominant type or abundance of carbon nanotube in the identifying mark is not needed to practice the embodiments of the present disclosure, simply that the distribution of carbon nanotube chiralities is known. However, in some embodiments, the plurality of carbon nanotubes can have one or more predominant types of carbon nanotubes, as this feature can prove advantageous for detection purposes. Various configurations in which the plurality of carbon nanotubes includes a predominant carbon nanotube type are discussed below.

The native distribution of carbon nanotube types in a non-specific carbon nanotube synthetic process is usually about ⅔ semiconducting carbon nanotubes and about ⅓ metallic carbon nanotubes. In some embodiments, the plurality of carbon nanotubes forming the identifying mark can have a higher percentage of semiconducting carbon nanotubes than is natively obtained from a non-specific carbon nanotube synthetic process. Illustrative techniques for producing enriched semiconducting carbon nanotubes are discussed above. In some embodiments, the plurality of carbon nanotubes can include about 70% semiconducting carbon nanotubes or more. In other various embodiments, the plurality of carbon nanotubes can include about 75% semiconducting carbon nanotubes or more, or about 80% semiconducting carbon nanotubes or more, or about 85% semiconducting carbon nanotubes or more, or about 90% semiconducting carbon nanotubes or more, or about 95% semiconducting carbon nanotubes or more. In some embodiments, the plurality of carbon nanotubes can include substantially only semiconducting carbon nanotubes. Illustrative semiconducting carbon nanotube chiralities that can be present in the identifying marks of the present disclosure include, for example, (1,0), (2,0), (4,0), (5,0), (7,0), (8,0), (10,0), (11,0), (13,0), (14,0), (16,0), (2,1), (3,1), (5,1), (6,1), (8,1), (9,1), (11,1), (12,1), (14,1), (15,1), (3,2), (4,2), (6,2), (7,2), (9,2), (10,2), (12,2), (13,2), (15,2), (4,3), (5,3), (7,3), (8,3), (10,3), (11,3), (13,3), (14,3), (5,4), (6,4), (8,4), (9,4), (11,4), (12,4), (14,4), (6,5), (7,5), (9,5), (10,5), (12,5), (13,5), (7,6), (8,6), (10,6), (11,6), (13,6), (8,7), (9,7), (11,7), (12,7), (9,8), (10,8), (12,8), (10,9), (11,9), and (11,10). Certain chiralities can be predominant in some carbon nanotube synthetic processes, as discussed in more detail below.

Likewise, in some embodiments, the plurality of carbon nanotubes can include a higher percentage of metallic carbon nanotubes than is natively obtained from a non-specific carbon nanotube synthetic process. In some embodiments, the plurality of carbon nanotubes can include about 50% metallic carbon nanotubes or more. In other various embodiments, the plurality of carbon nanotubes can include about 60% metallic carbon nanotubes or more, or about 70% metallic carbon nanotubes or more, or about 80% metallic carbon nanotubes or more, or about 90% metallic carbon nanotubes or more. In some embodiments, the plurality of carbon nanotubes can include substantially only metallic carbon nanotubes. In some embodiments, the plurality of carbon nanotubes can include substantially only functionalized metallic carbon nanotubes. Illustrative metallic carbon nanotubes that can be present in the identifying marks of the present disclosure include, for example, (3,0), (6,0), (9,0), (12,0), (15,0), (4,1), (7,1), (10,1), (13,1), (5,2), (8,2), (11,2), (14,2), (6,3), (9,3), (12,3), (7,4), (10,4), (13,4), (8,5), (11,5), (9,6), (12,6), (10,7), and (11,8).

As discussed above, it is not a necessary feature that the plurality of carbon nanotubes forming the identifying mark contains one or more predominant types of carbon nanotubes, simply that the plurality of carbon nanotubes has a registered distribution of carbon nanotube chiralities, where the abundances of one or more chiralities are known. However, in some embodiments, it can be desirable that the plurality of carbon nanotubes contains one or more carbon nanotube chiralities in a defined excess relative to the other carbon nanotube chiralities. By having one or more types of carbon nanotubes present in a significant abundance over the others, increased signal strength can result in improved detection accuracy (e.g., in a fluorescence spectrum or a Raman spectrum of the identifying mark).

In more specific embodiments, the identifying mark can contain a plurality of carbon nanotubes in which at least about 30% of the carbon nanotubes are of a single chirality. In some embodiments, at least about 50% of the carbon nanotubes can be of a single chirality, or at least about 70% of the carbon nanotubes can be of a single chirality. In some embodiments, the plurality of carbon nanotubes can contain a mixture of semiconducting and metallic carbon nanotubes in which a single chirality is present within the above ranges of abundance. In other various embodiments, the plurality of carbon nanotubes can include substantially only semiconducting carbon nanotubes or substantially only metallic carbon nanotubes in which a single chirality is present within the above ranges of abundance. The single carbon nanotube chirality that is present in the above ranges of abundance is not believed to be particularly limited, but can represent a carbon nanotube chirality that is readily produced in a particular carbon nanotube synthetic process. Illustrative carbon nanotube chiralities that can represent a predominant chirality in this regard include, for example, (6,5), (7,5), and (8,4) chiralities. In an illustrative embodiment, the plurality of carbon nanotubes can be a commercial carbon nanotube product containing about 90-97% semiconducting carbon nanotubes, which includes about 30-45% (6,5) carbon nanotubes and smaller quantities of (7,5) and (8,4) carbon nanotubes. Such a population of carbon nanotubes is available from SouthWest Nanotubes (Norman, Okla.) as product SG65i. In another illustrative embodiment, the plurality of carbon nanotubes can be a commercial carbon nanotube product containing greater than about 50% semiconducting carbon nanotubes of (7,6) chirality. Such a population of carbon nanotubes is available from SouthWest Nanotubes as product SG76. As discussed above, these carbon nanotube products can be used directly to form identifying marks, or they can be combined in any ratio to create a chirality distribution that is not found in either product. Other strategies for manipulating the distribution of carbon nanotube chiralities are discussed in further detail above. Other techniques for adjusting the spectroscopic signature of the identifying marks of the present disclosure are also described below.

Carbon nanotube lengths and diameters can also be varied as another parameter defining the identifying marks described herein. In some embodiments, an average length of the carbon nanotubes in the identifying mark can range between about 1 µm and about 500 µm, or between about 1 µm and about 10 µm, or between about 10 µm and about 100 µm, or between about 100 µm and about 200 µm, or between about 200 µm and about 300 µm, or between about 300 µm and about 400 µm, or between about 400 µm and about 500 µm. In other embodiments, the carbon nanotubes in the identifying mark can have an average length that is greater than about 500 µm, including, for example, between about 500 µm and about 700 µm, or between about 700 µm and about 1000 µm.

In some embodiments, the carbon nanotubes in the identifying mark can have diameters ranging between about 1 nm and about 20 nm. In more particular embodiments, the carbon nanotubes in the identifying mark can have diameters ranging between about 1 nm and about 10 nm, or between about 1 nm and about 7 nm, or between about 1 nm and about 5 nm, or between about 2 nm and about 6 nm, or between about 2 nm and about 5 nm, or between about 3 nm and about 8 nm. In some embodiments, the carbon nanotubes can be predominantly single-walled carbon nanotubes. In other embodiments, double-walled or multi-walled carbon nanotubes can be present. In some embodiments, mixtures of single-walled carbon nanotubes and double- or multi-walled carbon nanotubes can be used. In some embodiments, mixtures of two or more carbon nanotube types, each having different diameters, can be present in order to further tailor the spectroscopic fingerprint of the identifying marks described herein.

Semiconducting carbon nanotubes can be particularly desirable for use in conjunction with the embodiments described herein, since they are readily detectable in low abundance using fluorescence spectroscopy, and the frequency of the fluorescence is correlatable to the specific carbon nanotube chiralities that are present. Further details of the fluorescence properties of semiconducting carbon nanotubes and their associated chirality assignments can be found in Bachilo, et al., "Structure-assigned optical spectra of single-walled carbon nanotubes," Science, 298:2002, pp. 2361-2366.

Carbon nanotubes can also be readily detected and analyzed in the solid state using Raman spectroscopy, such as a microtiter plate format for rapid analyses. Unlike fluorescence spectroscopy, which is only workable for semiconducting carbon nanotubes, Raman spectroscopy can be used to detect and analyze both metallic and semiconducting carbon nanotubes. As with fluorescence spectroscopy, the excitation frequencies of a Raman spectrum can be correlated with the particular carbon nanotube chiralities that are present in the sample being analyzed. The diameters of the carbon nanotubes can also be readily determined from a Raman spectrum, and the carbon nanotube diameters in the identifying mark can serve as another level of security against unwanted counterfeiting by an outside entity. As mentioned above, optical reflectivity can also be used to provide an additional level of security in a similar manner.

An alternative analysis strategy for assaying an identifying mark formed from carbon nanotubes can include resistance monitoring techniques. However, it is believed that the foregoing spectral analysis techniques are superior to resistance monitoring, particularly from a security standpoint. Foremost, resistance monitoring techniques provide no effective means to identify the particular carbon nanotube chiralities that are present in a plurality of carbon nanotubes. Moreover, the resistance of a carbon nanotube mat can be matched in many instances simply by increasing or decreasing the thickness of the mat, irrespective of the types or chiralities of carbon nanotubes or other carbon nanomaterials that are present. Thus, it is believed that resistance measurements can be replicated fairly easily by an outside entity attempting to produce a counterfeit mark. As described herein, the particular distribution of carbon nanotube chiralities in a plurality of carbon nanotubes can be much more difficult for an outside entity to replicate. Further, because the marks described herein are not visible to the naked eye due to the scant quantities of carbon nanotubes or other carbon nanomaterials present therein, they are not believed to be particularly suitable for analysis by resistance monitoring techniques.

As mentioned above, the identifying marks described herein can contain a nanomaterial that includes a plurality of carbon nanotubes having a registered distribution of chiralities. In some embodiments, other carbon nanomaterials such as graphene, nanocarbon particles, or nanodiamond can be used in any combination with carbon nanotubes in the identifying marks described herein. In alternative embodiments, the foregoing nanomaterials can be used separately or in combination with one another, but without carbon nanotubes being present, to form an identifying mark with a distinctive spectral signature that makes the identifying mark spectroscopically identifiable. For example, in some embodiments, an identifying mark can be formed from graphene, nanodiamond, or a mixture of graphene and nanodiamond. One of ordinary skill in the art will recognize that these nanomaterials also possess characteristic spectral signatures that can be used to validate an identifying mark according to the embodiments described herein.

Figure 3A:
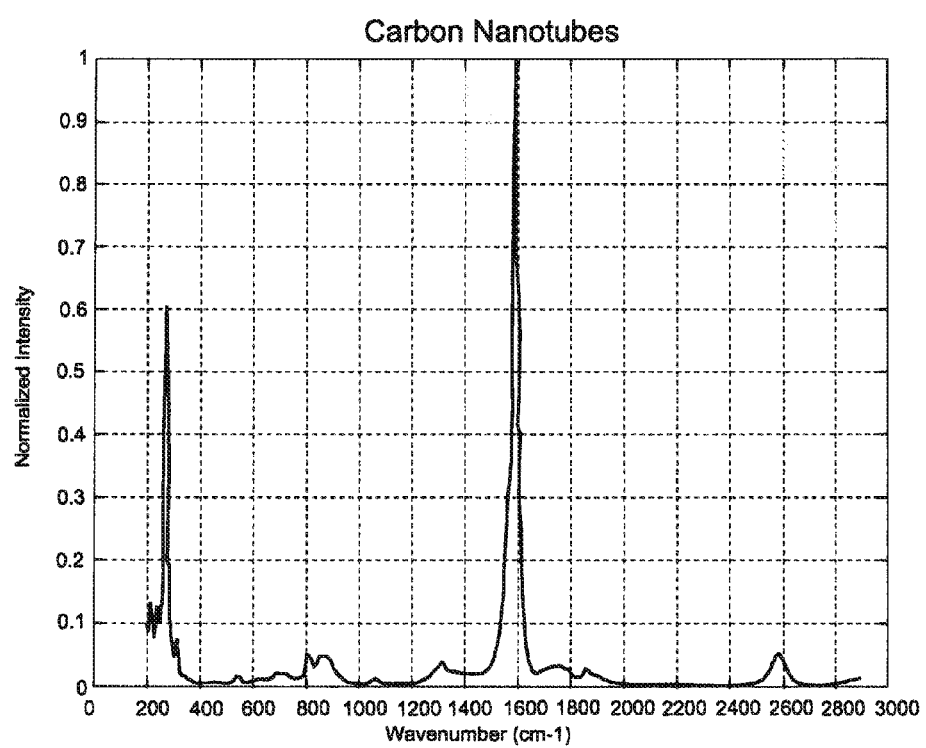
FIGS. 3A-3C show a comparison between illustrative Raman spectra for carbon nanotubes, rubrene (5,6,11,12-tetraphenyltetracene), and carbon nanotubes that have been mixed with rubrene.
Figure 3B:
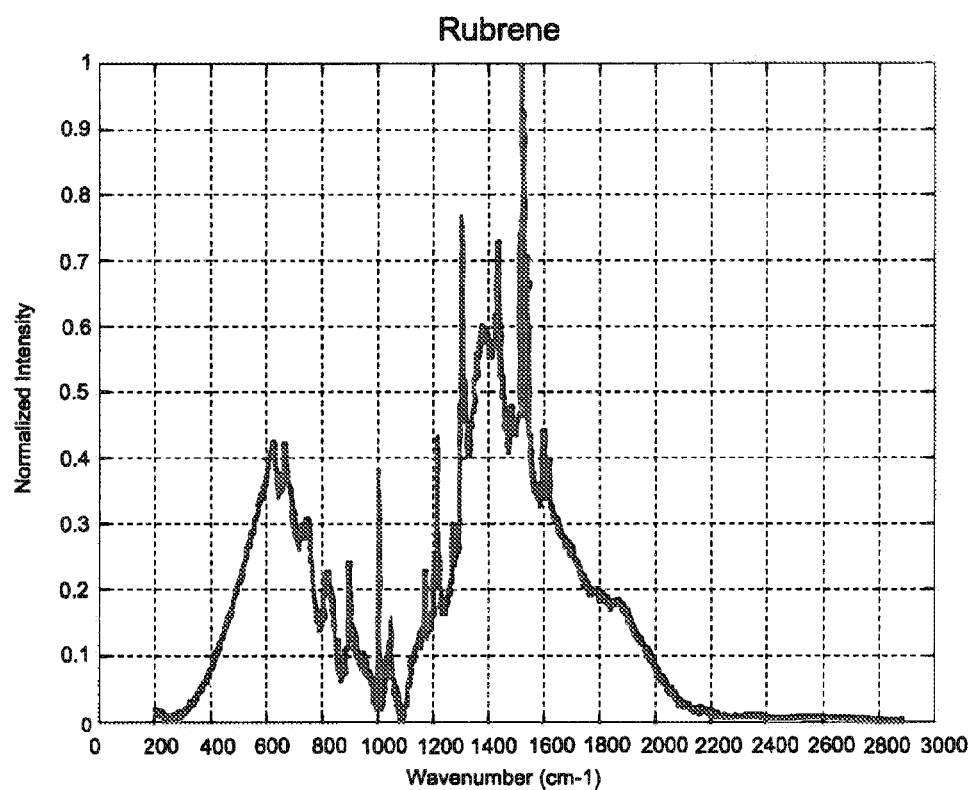
Figure 3C:
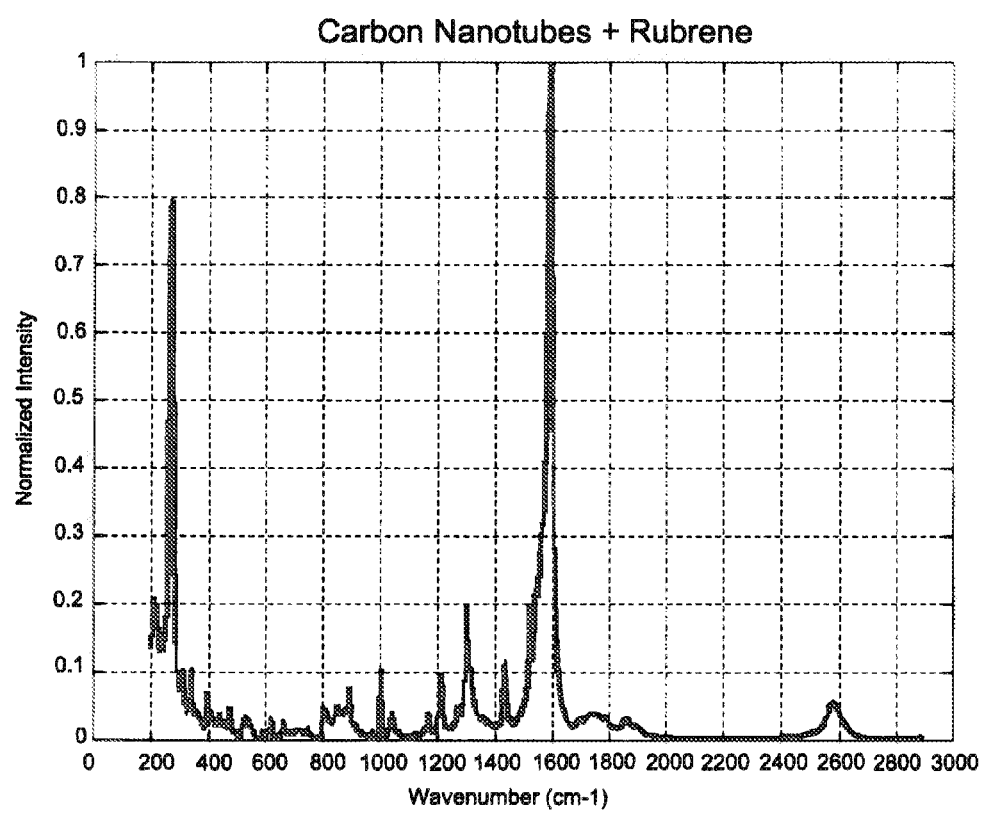
Figure 4A:
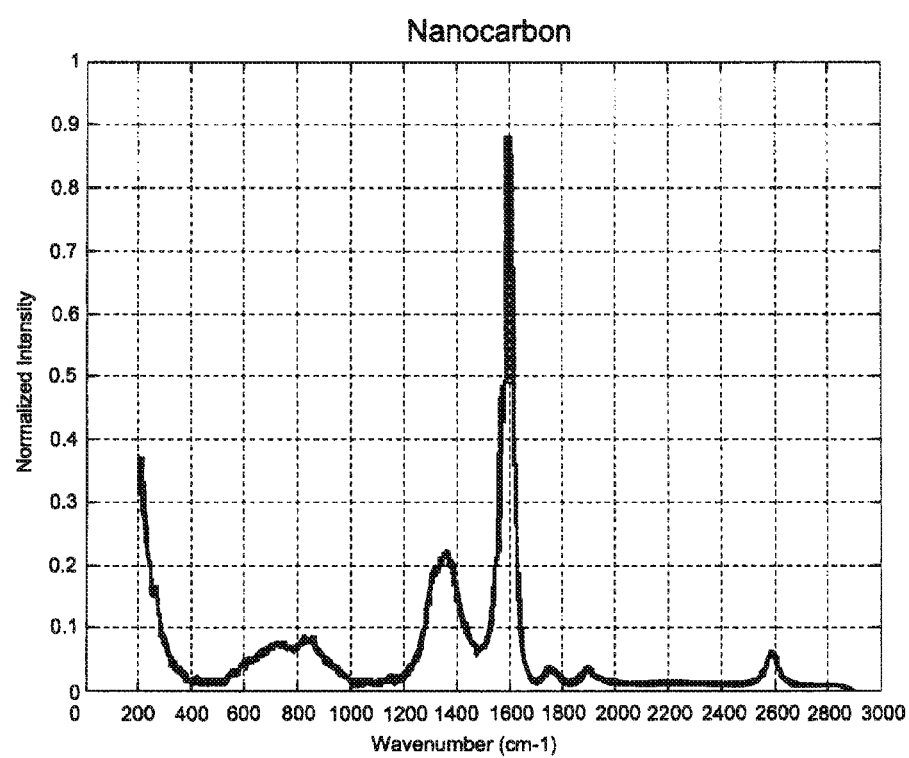
FIGS. 4A-4C show a comparison between illustrative Raman spectra for nanocarbon, rubrene, and nanocarbon mixed with rubrene.
Figure 4B:
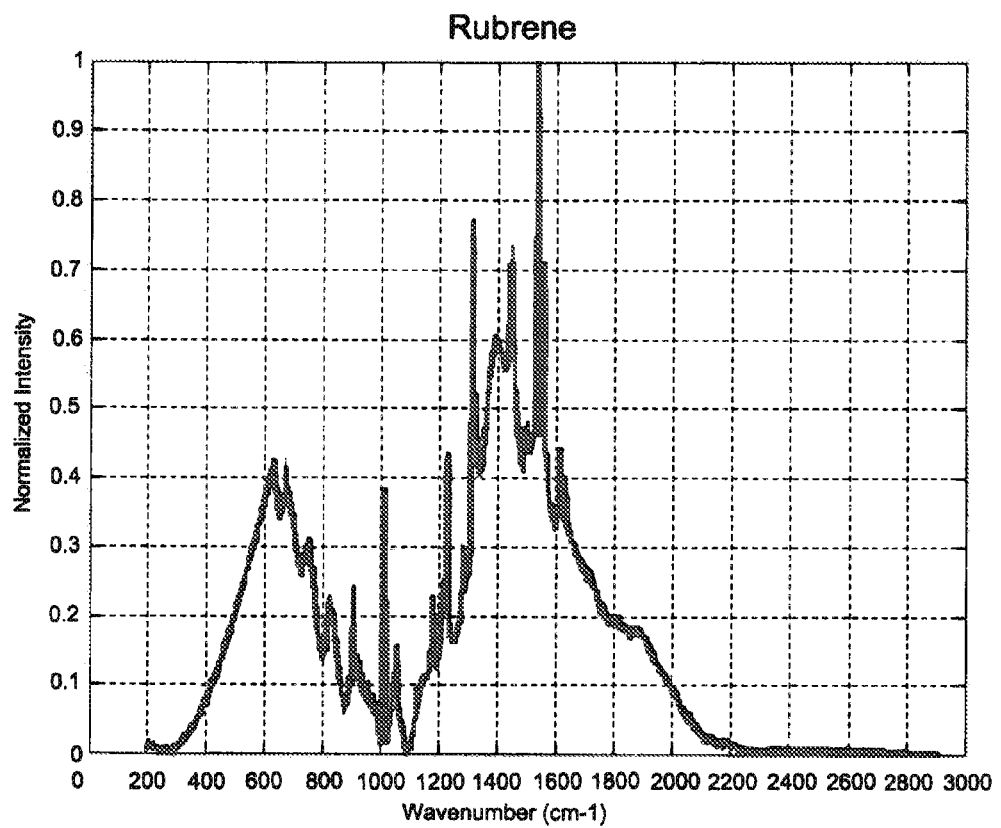
Figure 4C:
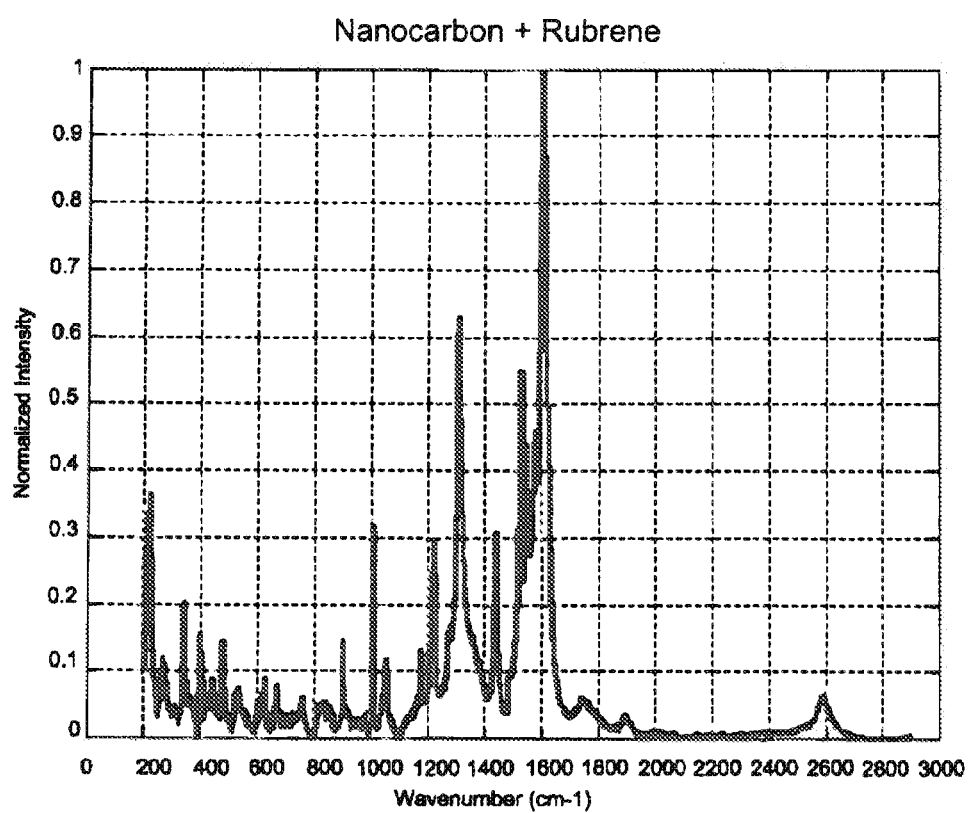

In addition to other carbon nanomaterials, other carbonaceous materials can also be present in the identifying marks described herein. Suitable carbonaceous materials that can be included in the identifying marks described herein include, for example, graphite, various polymers, aromatic hydrocarbons, particularly polycyclic aromatic hydrocarbons, and the like. These materials can likewise be used to influence the spectral signature obtained from carbon nanotubes or another carbon nanomaterial. FIGS. 3A-3C show a comparison between illustrative Raman spectra for carbon nanotubes, rubrene (5,6,11,12-tetraphenyltetracene), and carbon nanotubes that have been mixed with rubrene. FIGS. 4A-4C similarly show a comparison between illustrative Raman spectra for nanocarbon, rubrene, and nanocarbon mixed with rubrene. As can be seen from the comparative spectra, the rubrene imparts a distinctive spectral signature that is not present in the undoped nanomaterial spectra.

As an additional means of protecting the identifying marks described herein, both from the marks' external environment as well as unwanted investigation by an outside entity, the articles described herein can further include a coating covering at least the identifying mark. In general, any spectroscopically transparent film that adheres to the article and prevents or inhibits damage to or reaction of the identifying mark, removal of the identifying mark, or investigation of the identifying mark can be used in accordance with the embodiments described herein. That is, coatings suitable for use in accordance with the embodiments described herein can include substances that are not appreciably Raman active or fluorescent, at least within the frequency range over which the carbon nanotubes in the identifying mark are Raman active or fluorescent. Various polymer films can be used as a coating on the articles described herein, a number of which will be familiar to one having ordinary skill in the art. Choice of a suitable polymer film for forming the coating can be dictated by factors including, for example, the degree to which the polymer film adheres to a particular article containing the identifying mark. Illustrative polymer films that can be used in conjunction with the embodiments described herein include, for example, polyimides, silicone polymers, polycarbonates, fluoropolymers such as polytetrafluoroethylene, and the like. In addition to protecting the identifying mark, as described above, the carbon present in the polymer film can further conceal the presence of carbon nanotubes in the article from an outside entity.

As an additional level of security, in some embodiments, multiple identifying marks can be present at different locations within the articles described herein. In some embodiments, each identifying mark can include a plurality of carbon nanotubes having a different registered distribution of chiralities. In other various embodiments, each mark or at least some of the identifying marks can include a plurality of carbon nanotubes having the same registered distribution of chiralities. In either case, in order for an outside entity to reproduce an article containing the identifying marks, the outside entity would need to both locate all the marks and replicate their particular distribution of carbon nanotube chiralities. In some embodiments, the identifying marks can be integrated into any layer of the article, and can be used to create marks at various levels for a multilayered architecture that further increases the complexity of the marking process. In some embodiments, the identifying marks can be located within one or more layers of the article, when the article contains one or more layers. When present in multiple layers, the identifying marks can contain the same carbon nanotube chirality distribution in each layer, or different carbon nanotube chirality distributions can be present in at least some of the layers. The patterning of the identifying marks within each layer can also be the same or different. Moreover, in some embodiments, different carbon nanomaterials can be present with the marks within at least some of the layers.

In additional embodiments where multiple identifying marks are present within an article, such marks can be formed into a one-dimensional or two-dimensional array of adjacent marks corresponding to two or more identifying spectral signatures. In these embodiments, the security level of the mark can be increased because such configurations further necessitate spatially mapping the spectral output of the mark and correlating both the dimension and spectrum of each segment within the mark. For example, a bar code or other identifying mark can be generated from two or more carbon nanotube sources, each with a registered chirality distribution, where each carbon nanotube source is used to form only a portion of the mark or the two or more carbon nanotube sources are combined within only a portion of the mark. In this case, Raman interrogation can be used to scan across the mark as the spectral signature is captured as a function of position and geometry within the mark. The validation of the mark then represents a function of both the location and width of each spectral signature, as well as the particular spectral features themselves.

In various embodiments, methods for marking an article with carbon nanotubes and thereafter tracking the article are described herein. In some embodiments, methods described herein can include: providing an article in need of tracking; applying an identifying mark to a surface of the article, the identifying mark not being visible to the naked eye and containing a nanomaterial that includes a plurality of carbon nanotubes having a registered distribution of chiralities; operationally deploying the article; and after operationally deploying the article, optically interrogating the article with electromagnetic radiation to assay the identifying mark. As described above, the registered distribution of chiralities can be known to a manufacturer or a supplier of an article, but not to an end user or other outside entity who may wish to replicate the article, thereby providing improved protection for the manufacturer or supplier against theft and production of counterfeit copies of the article. In addition to or as an alternative of carbon nanotubes, other carbon nanomaterials can be used similarly in this regard. as described herein.

In some embodiments, optically interrogating the article can include obtaining a fluorescence spectrum or a Raman spectrum of the identifying mark. In some embodiments, both a fluorescence spectrum and a Raman spectrum can be obtained to fully characterize the distribution of carbon nanotube chiralities in the identifying mark (i.e., to show the distribution of metallic carbon nanotube chiralities relative to semiconducting carbon nanotube chiralities). In further embodiments, the relative peak intensities of the fluorescence spectrum can be compared to those of the Raman spectrum to verify that overlapping peaks are not present in the Raman spectrum. In some or other embodiments, optically interrogating the article can include obtaining the optical reflectance of the identifying mark, or assaying the non-linear optical properties of the mark.

In some embodiments, methods described herein can include comparing the fluorescence spectrum and/or Raman spectrum produced upon optical interrogation of the identifying mark and comparing the spectrum/spectra to the registered distribution of carbon nanotube chiralities in the plurality of carbon nanotubes originally used to apply the mark. That is, in some embodiments, the methods described herein can include determining a distribution of carbon nanotube chiralities in the identifying mark from the fluorescence spectrum or the Raman spectrum, and comparing the distribution of carbon nanotube chiralities to the registered distribution of chiralities in the plurality of carbon nanotubes used to apply the identifying mark to the article. If the two chirality distributions match within experimental error, as well as the mark's expected physical location and dimensions within the article, the article can be confirmed with some certainty as being authentic. If the two chirality distributions measurably differ, or if the identifying mark otherwise unexpectedly differs in configuration or position, further investigation into the authenticity of the article may be needed. Although unlikely, non-matching chirality distributions need not necessarily indicate the presence of a counterfeit article. For example, environmental conditions (e.g., chemicals, ultraviolet radiation, and the like) can measurably change the spectral fingerprint of an authentic identifying mark over time to a sufficient degree to bring the article's authenticity into question. Various means can be used to protect the carbon nanotubes from unwanted environmental conditions or other factors, as generally discussed above. For example, in some embodiments, a coating can be applied to the article to protect the identifying mark or to provide additional functions. Specifically, in some embodiments, methods described herein can further include applying a coating onto the article that cover at least the identifying mark, where the coating still allows the article to be spectroscopically interrogated.

As discussed above, any population of carbon nanotubes having a registered distribution of chiralities can be used in accordance with the embodiments described herein. In some embodiments, the carbon nanotubes having a registered distribution of chiralities can include those produced from a carbon nanotube synthetic process, optionally following purification of the carbon nanotubes.

In some or other embodiments, the methods described herein can include formulating the plurality of carbon nanotubes to have a non-native distribution of carbon nanotube chiralities. Formulating the plurality of carbon nanotubes to have a non-native distribution of carbon nanotube chiralities can be accomplished in several different manners, as described in more detail above. In still other embodiments, at least a portion of the carbon nanotubes can be functionalized, as also described above.

In various embodiments, applying an identifying mark to an article can further include preparing or obtaining a solution or suspension of carbon nanotubes having a registered distribution of carbon nanotube chiralities. In general, any solvent that provides good dispersion or solubilization of the carbon nanotubes can be used in accordance with the present embodiments. Various surfactants can also be used in conjunction with the solvent in this regard. In more particular embodiments, the solvent used in conjunction with applying the identifying mark to the article can represent a volatile solvent, which can aid in its removal from the article by evaporation following application of the mark. Applying the solution or suspension of carbon nanotubes to the article can take place by any suitable technique. In various embodiments, application of the carbon nanotubes to the article to produce the identifying mark can take place by spray coating, spin coating, printing, or any combination thereof. In some embodiments, these techniques can be used to produce substantially a monolayer of carbon nanotubes on the surface of the article.

Although the invention has been described with reference to the disclosed embodiments, those skilled in the art will readily appreciate that these only illustrative of the invention. It should be understood that various modifications can be made without departing from the spirit of the invention. The invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description.

What is claimed is the following:

1. An article comprising:
an identifying mark that is not visible to the naked eye, the identifying mark comprising a nanomaterial that includes a plurality of carbon nanotubes having a registered distribution of chiralities and at least one other nanomaterial selected from the group consisting of a population of carbon nanotubes having a different distribution of chiralities, graphene and nanodiamond.

2. The article of claim 1, wherein the plurality of carbon nanotubes comprises as-produced carbon nanotubes obtained from a carbon nanotube synthetic process.

3. The article of claim 1, wherein the plurality of carbon nanotubes comprises a mixture of carbon nanotubes combined from a first carbon nanotube synthetic process and a second carbon nanotube synthetic process, the first and second carbon nanotube synthetic processes producing carbon nanotubes that differ in at least their distribution of chiralities.

4. The article of claim 1, wherein the plurality of carbon nanotubes comprises carbon nanotubes having one or more chiralities that have been enriched from as-produced carbon nanotubes obtained from a carbon nanotube synthetic process.

5. The article of claim 1, wherein at least a portion of the plurality of carbon nanotubes are functionalized.

6. The article of claim 1, wherein the plurality of carbon nanotubes comprises about 70% semiconducting carbon nanotubes or more.

7. The article of claim 1, wherein at least about 30% of the carbon nanotubes are of a single chirality.

8. The article of claim 1, further comprising:
a coating covering at least the identifying mark.

9. The article of claim 1, wherein the article comprises an electrical device.

10. The article of claim 9, wherein the plurality of carbon nanotubes comprises at least a portion of a conductive line in a circuit of the electrical device.

11. The article of claim 1, wherein the identifying mark comprises substantially a monolayer of carbon nanotubes on a surface of the article.

12. The article of claim 1, wherein multiple identifying marks are present at different locations within the article.

13. The article of claim 12, wherein each identifying mark comprises a plurality of carbon nanotubes having a different registered distribution of chiralities.

14. The article of claim 12, wherein the article comprises multiple layers, and the multiple identifying marks are located within more than one layer of the article.

15. A method comprising:
providing an article in need of tracking;
applying an identifying mark to a surface of the article, the identifying mark not being visible to the naked eye and comprising a nanomaterial that includes a plurality of carbon nanotubes having a registered distribution of chiralities and further comprising at least one other nanomaterial selected from the group consisting of a population of carbon nanotubes having a different distribution of chiralities, graphene and nanodiamond;
operationally deploying the article; and
after operationally deploying the article, optically interrogating the article with electromagnetic radiation to assay the identifying mark by obtaining a Raman spectrum.

\* \* \* \* \*